(12) United States Patent
Brittain et al.

(10) Patent No.: US 7,693,569 B1
(45) Date of Patent: Apr. 6, 2010

(54) METHOD AND SYSTEM OF DETERMINING MOTION IN A REGION-OF-INTEREST DIRECTLY AND INDEPENDENTLY OF K-SPACE TRAJECTORY

(75) Inventors: Jean H. Brittain, Menlo Park, CA (US); Anja C. S. Brau, Menlo Park, CA (US)

(73) Assignee: General Electric Company, Schenectady, NY (US)

(*) Notice: Subject to any disclaimer, the term of this patent is extended or adjusted under 35 U.S.C. 154(b) by 810 days.

(21) Appl. No.: 10/711,892

(22) Filed: Oct. 12, 2004

(51) Int. Cl.
*A61B 5/05* (2006.01)

(52) U.S. Cl. .................. 600/413; 600/407; 600/410; 324/307; 324/309

(58) Field of Classification Search ............. 600/413; 324/307, 309
See application file for complete search history.

(56) References Cited

U.S. PATENT DOCUMENTS

| | | | |
|---|---|---|---|
| 4,564,017 A | 1/1986 | Glover | |
| 4,961,426 A | 10/1990 | Spraggins et al. | |
| 2003/0216637 A1* | 11/2003 | Ho et al. | 600/415 |
| 2004/0155653 A1* | 8/2004 | Larson et al. | 324/309 |

OTHER PUBLICATIONS

Haacke, E. M. et al, Magnetic Resonance Imaging, 1999, John Wiley and Sons, p. 796.*
Pipe, James G., "Motion Correction With PROPELLER MRI: Application to Head Motion and Free-Breathing Cardiac Imaging," Magnetic Resonance in Medicine 42:963-969 (1999).*
Crowe et al., Automated Rectilinear Self-Gated Cardiac Cine Imaging, Magnetic Resonance in Medicine 52:782-788 (2004).
Xiaping Hu et al., Reduction of Signal Fluctuation in Functional MRI Using Navigator Echoes, pp. 495-503 (1994).
Ehman et al., "Adaptive Technique for High-Definition MR Imaging of Moving Structures," Magnetic Resonance Imaging, vol. 173, No. 1, Oct. 1989, pp. 255-263.

* cited by examiner

*Primary Examiner*—Brian Casler
*Assistant Examiner*—John F Ramirez
(74) *Attorney, Agent, or Firm*—Ziolkowski Patent Solutions Group, SC

(57) ABSTRACT

A system and method for determining motion in a region-of-interest directly from MR data acquired from the region-of-interest and independently of k-space trajectory are disclosed.

20 Claims, 9 Drawing Sheets

METHOD AND SYSTEM OF DETERMINING MOTION IN A REGION-OF-INTEREST DIRECTLY AND INDEPENDENTLY OF K-SPACE TRAJECTORY

BACKGROUND OF THE INVENTION

The present invention relates generally to MR imaging and, more particularly, to a method and system of determining motion in a region-of-interest directly from MR data acquired from the region-of-interest independent of k-space trajectory of a k-space filling scheme carried out to sample the region-of-interest.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Any type of subject motion—cardiac, respiratory, or other body motion—during MRI may introduce image artifacts that affect the quality of an image and, ultimately, diagnostic utility of the scan. A number of techniques have been developed to reduce motion artifacts in MRI. One class of techniques synchronizes data acquisition with motion using breath-holding, respiratory triggering, and/or cardiac gating to "freeze" subject motion. Another class of techniques corrects data acquired in the presence of motion. Despite the use of these techniques, however, motion remains one of the primary impediments to diagnostic image quality.

Most known motion artifact reduction techniques require the ability to measure subject motion during the scan, either by external physical tools (e.g. respiratory bellows, electrocardiogram (ECG), pulse oximetry, and the like) or by interleaving extra gradient pulses into the pulse sequence (e.g. navigator echoes)—both of which impose additional time, cost, and complexity to the scan and scan system. Furthermore, external physical measurements are typically indirect, error-prone measures of motion that may not accurately reflect true motion in the region-of-interest. For example, respiratory bellows measure only the anterior-posterior component of breathing motion at the abdominal surface, while the ECG measures electrical rather than mechanical cardiac activity. While breath-holding can be used to minimize respiratory motion artifacts and does not require the ability to measure motion, it limits image quality, suffers from drift and position inconsistencies, and is often impractical in severely ill or pediatric subjects.

Other known motion assessment techniques are k-space trajectory limited. That is, one known technique determines motion in a region-of-interest directly from MR imaging data acquired from the region-of-interest. That is, this technique determines motion from spatially encoded data, rather than data acquired without spatial encoding. In this regard, this technique is severely limited in its applications. Simply, the technique is applicable only with spiral and radial sampling. As such, the technique cannot be used for MR scans in which resonance is sampled and k-space filled using non-spiral or non-radial k-space trajectories. As there are a number of MR imaging techniques that do not rely upon a spiral or radial k-space trajectory, this known technique, and others that are k-space trajectory limited, is frequently inapplicable.

Other proposed "self-navigated" techniques sample additional echoes that are generated without phase encoding. The data associated with these additional and fully-sampled echoes is then analyzed to determine motion in a region-of-interest. Since "extra" echoes must be induced and then sampled, such a technique can significantly lengthen scan time and increase the memory and processing requirements of an MR scanner.

It would therefore be desirable to have a system and method capable of more direct, efficient, and accurate measuring of motion in a region-of-interest that is independent of k-space trajectory such that motion artifact reduction techniques may be applied with greater success in many MR applications and without increasing scan time.

BRIEF DESCRIPTION OF THE INVENTION

The present invention is directed to a method and apparatus of assessing motion in a region-of-interest directly from MR data acquired from the region-of-interest independent of the k-space trajectory used to fill k-space that overcomes the aforementioned drawbacks.

The present invention is directed to the extraction of motion information within a region-of-interest directly from raw k-space data without implementation of separate physiological motion measuring systems. Moreover, by employing a direct extraction of motion information from k-space, the present invention provides a measurement of motion in the region-of-interest that is more accurate when compared to indirect techniques of assessing motion, i.e. ECGs. Additionally, the present invention is capable of ascertaining magnitude as well as phase information with respect to motion in a region-of-interest. In this regard, the present invention may be applied to not only improving synchronization of MR data in a gated acquisition, but also used in slice tracking and phase error correction. Furthermore, not only is the present invention k-space trajectory independent, it may also be implemented to assess multiple types of motion in a region-of-interest, such as respiratory, cardiac, and other anatomical induced motion. Moreover, the present invention is applicable with single coil and multi-coil receivers and, as such, can be used to differentiate location and direction of motion in an excited region based on coil sensitivity to the excited region. An understanding of location and direction of motion can further enable accurate assessment of motion in the region-of-interest for acquisition synchronization, slice tracking, and error correction.

The present invention is particularly applicable to body imaging scans where respiratory motion can severely limit image quality, especially in subjects who cannot hold their breath for extended periods of time. The present invention may also be applicable in cardiac imaging. In this regard, a separate ECG acquisition can be avoided and motion information derived directly from MR data can be used as a cardiac gating trigger for CINE imaging and other cardiac protocols. Detected respiratory motion of the heart could also be used to synchronize cardiac imaging with breathing or to perform slice tracking, particularly in coronary artery imaging applications, which are vulnerable to breathing motion.

Therefore, in accordance with one aspect of the invention, an MRI apparatus is disclosed and includes a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images. A computer is programmed to sample MR signals from a region-of-interest having motion therein with a given k-space trajectory to fill k-space and determine motion in the region-of-interest directly from sampled MR data acquired from the MR signals independent of the given k-space trajectory used to fill k-space and fill k-space with a k-space filling scheme that fills an origin of k-space at least once every repetition internal of a pulse sequence.

In accordance with another aspect, the present invention includes a method of MR imaging. The method includes sampling MR data over a plurality of repetition time intervals for a central region of k-space filled, using a given k-space filling trajectory, with MR data acquired from the region-of-interest having motion therein. The method also includes the steps of monitoring motion-induced modulation in the MR data for the central region of k-space over the plurality of repetition time intervals and determining motion in the region-of-interest from the motion-induced modulation independent of the given k-space filling trajectory.

According to another aspect, the present invention may be found in a computer readable storage medium having a computer program stored thereon to assess motion in a region-of-interest. The computer program includes a set of instructions that when executed by a computer causes the computer to sample a central region of k-space each repetition time interval of a pulse sequence applied to acquire MR data from the region-of-interest. The computer is then caused to measure modulation of MR data in the central region over several repetition time intervals. The computer is also caused to determine motion in the region-of-interest based on differences in magnitude and phase measured in the MR data over the several repetition time intervals independent of k-space trajectory used to sample the region-of-interest.

In accordance with yet another aspect, the present invention includes a method of MR imaging that includes acquiring a first set of non-spatially encoded MR data from a region-of-interest prior to application of spatially encoding gradients and acquiring a second set of non-spatially encoded MR data from the region-of-interest after application of rewinder gradients. Motion in the region-of-interest is then determined from the first and the second set of non-spatially encoded MR data.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 1:
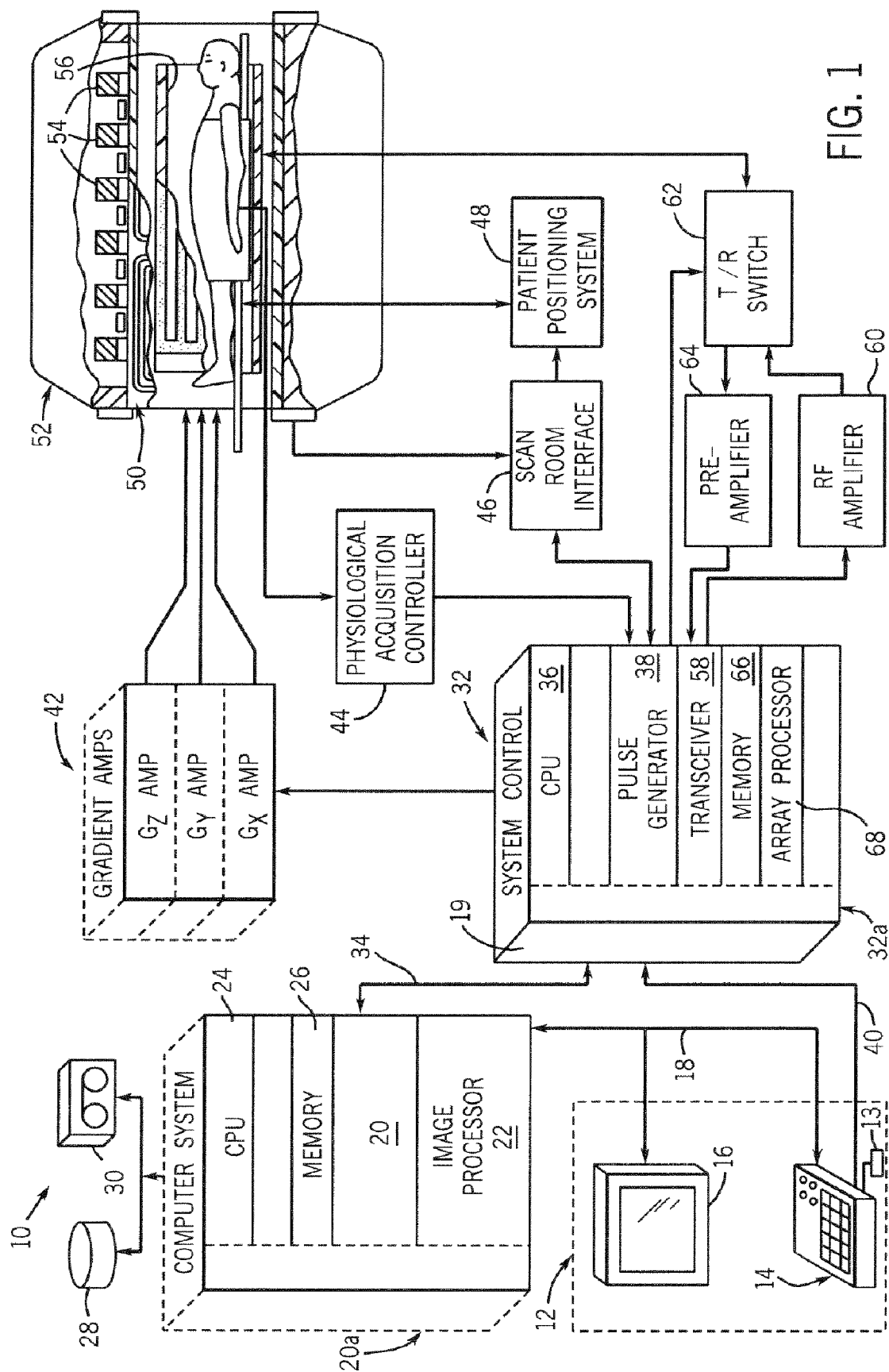
FIG. 1 is a schematic block diagram of an MR imaging system for use with the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

The present invention is directed a technique of assessing of motion in a region-of-interest directly from MR data acquired from the region-of-interest and independently of k-space trajectory of a k-space filling strategy that may be implemented on the MRI apparatus illustrated in FIG. 1, or equivalent thereof.

The present invention determines motion in a region-of-interest directly from MR data acquired from the region-of-interest without additional physiological motion measuring devices or additional gradient pulses. This extracted data may then be used in a number of motion artifact reduction techniques predicated upon knowledge of the amount and type of motion in the region-of-interest including, but not limited to synchronization of image acquisition with motion or the correction of data acquired in the presence of motion. The present invention is applicable with stationary and moving table MRI, including incremental and continuous moving table MRI.

Most pulse sequences excite, encode, and readout data from a region-of-interest with a k-space trajectory that passes through the origin of k-space at least once every repetition time interval. Given that the data at the k-space origin represents the integrated intensity of all transverse magnetization in an excited region, area, or volume-of-interest, any change or modulation experienced in the MR data of the k-space origin over time can be attributed to motion-induced changes in magnetization, assuming steady-state conditions. For example, in cardiac imaging, changes in myocardial wall thickness and blood volume over the cardiac cycle cause periodic fluctuations in transverse magnetization. In body imaging, changes in the position of the lung, diaphragm, and liver due to breathing can cause in-plane and/or through-plane movement that modulates magnetization. These effects can be assessed directly from the MR data in light of magnitude and phase modulation caused to the MR data at the k-space origin independently of k-space trajectory using a "self-navigated" technique described herein. As a "self-navigated" technique, the present invention does not require additional gradient pulses to extract motion data from a region-of-interest.

Figure 2:
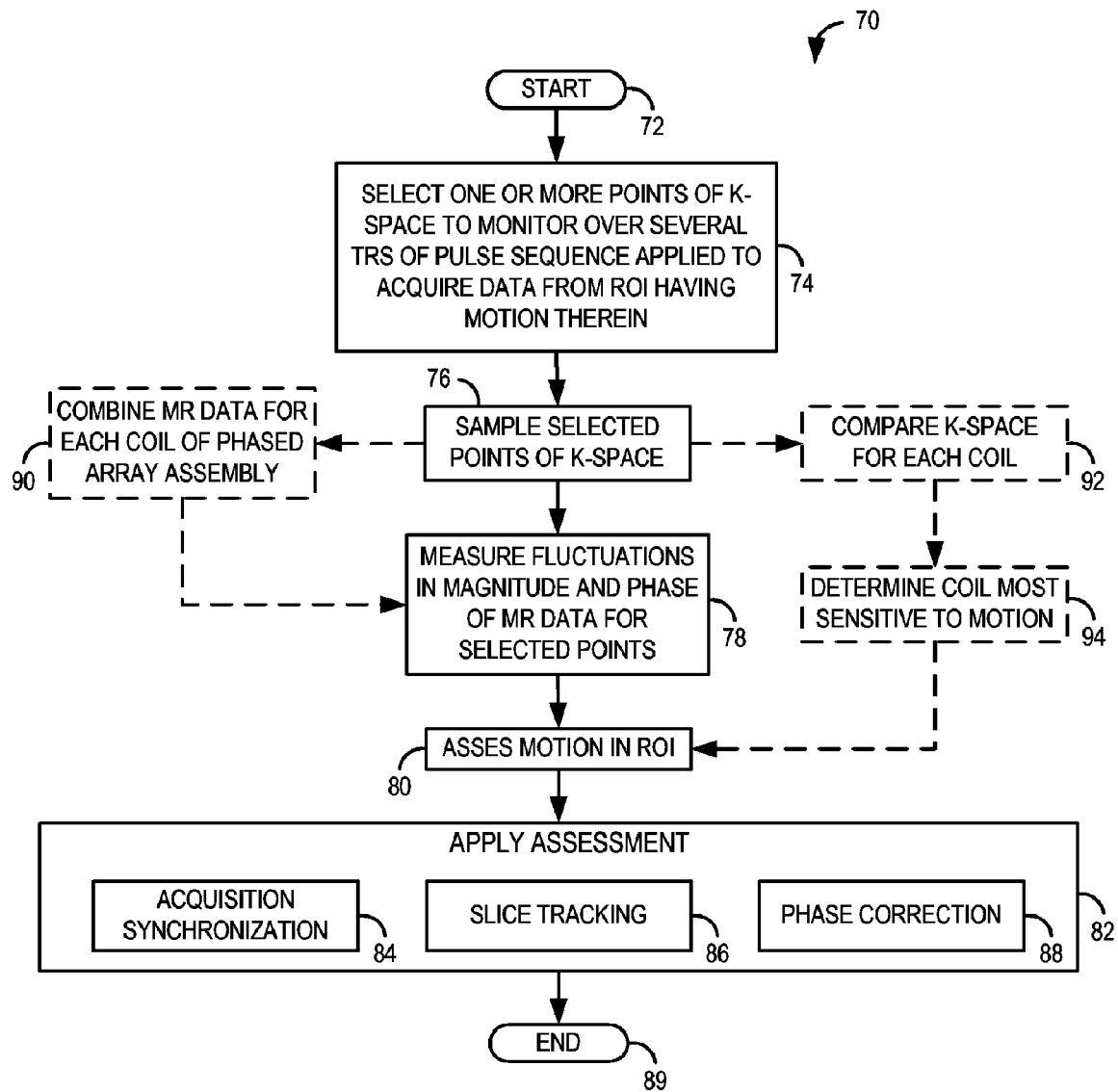
FIG. 2 is a flow chart setting forth the steps of a motion-assessment and application technique in accordance with the present invention.

Referring now to FIG. 2, a flow chart setting forth one embodiment of the present invention is shown. Process 70 begins at 72 with user input of scan parameters defining a pulse sequence for data acquisition of a region-of-interest in a conventional manner. Following setting up the particulars of the scan, one or more points about the k-space origin are selected for monitoring of motion-induced fluctuations 74. The one or more points, which are preferably centered about and include the k-space origin, are sampled over several repetition time intervals of the pulse sequence 76. By sampling the selected points of k-space over several cycles, fluctuations in the MR data corresponding thereto can be readily ascertained at 78. In a preferred embodiment, fluctuations in both the magnitude and the phase of the sampled MR data will be measured and used to assess the scope and extent of motion in the region-of-interest 80.

The assessment of the motion in the region-of-interest can be applied in a number of ways 82. The magnitude may be used to define cardiac and/or respiratory cycles. With an understanding to the cardiac and/or respiratory cycles, the motion information determined at 80 may be used to synchronize a gated MR data acquisition 84 to improve signal-to-noise and contrast-to-noise. In addition, the magnitude of motion-induced fluctuations in the data for the k-space origin can also be used to carry out slice tracking 86. Additionally, the phase of motion-induced fluctuations can be used for correcting phase errors 88 in acquired MR data to reduce image artifacts and improve image quality, whereupon the process ends at 89. One skilled in the art will appreciate that synchronization, slice tracking, and phase error correction are just three motion related processes to which the motion information determined from the region-of-interest may be applicable and that is contemplated that the present invention may be applicable with other motion artifact reduction techniques.

It is contemplated that synchronization, slice tracking, and phase error correction can be carried out prospectively or retrospectively. That is, it is contemplated that a fast scout scan can be carried out to acquire MR data from a region-of-interest. The MR data can then be assessed, as described herein, to determine motion in the region-of-interest and the motion information learned can be used to define the parameters of a subsequent and full imaging scan. On the other hand, a full imaging scan can be carried out and data in or about the origin of k-space can be accessed prior to image reconstruction to determine motion in the region-of-interest. From the motion information, data may be realigned relative to determined motion in the region-of-interest prior to image reconstruction so as to reduce ghosting and other artifacts in the reconstructed image.

Referring again to FIG. 2, the present invention is applicable with single coil and multi-coil receivers. For a multiple coil assembly, each coil has a sensitivity to a region-of-interest that varies between the coils based on the spatial proximity of each coil to the region-of-interest. Further, as each coil separately samples signal from the region-of-interest and the sampled data is used to fill a corresponding k-space matrix for each coil, the present invention contemplates that the data for selected points of k-space can be combined at 90 from the k-space matrices of the multiple coils to assess motion in the region-of-interest 78. That is, fluctuations in magnitude and phase of the k-space data is determined from a composite set of k-space data derived from k-space data acquired by all the coils of the multi-coil assembly, e.g. phased array architecture. On the other hand, it is contemplated that the k-space data from the multiple k-space matrices can be compared to one another 92 to determine a coil most sensitive to motion in the region-of-interest 94. The motion information derived from the k-space of the coil most sensitive to motion in the region-of-interest is then used to assess motion in the region-of-interest and subsequent application in motion artifact reduction processes. The coil most sensitive to motion in the region-of-interest may be determined from which k-space origin has the greatest fluctuations in magnitude and/or phase of corresponding MR data.

Figure 3:
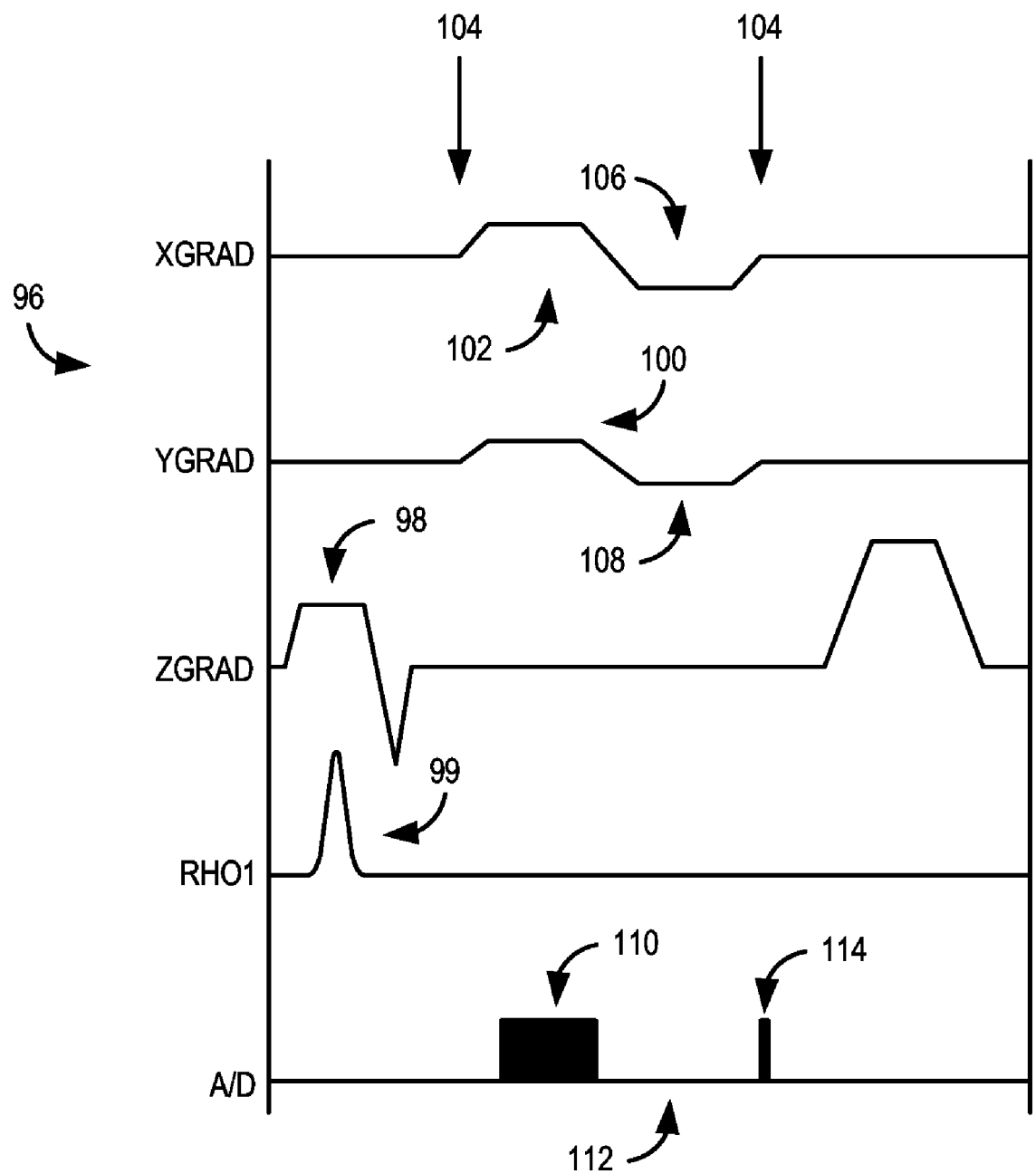
FIG. 3 is a pulse sequence diagram incorporating the present invention with a radial center-out k-space trajectory.

Referring now to FIG. 3, a pulse sequence diagram illustrates application of the present invention with acquisition of MR data from a region-of-interest using a radial center-out k-space filling scheme. Pulse sequence 96 is defined by a slice select gradient 98 played on in the presence of an excitation pulse 99, a phase encoding gradient 100, and a frequency encoding gradient 102. Arrows 104 indicate the instant at which the origin of k-space is traversed. In this regard, traversal of the origin of k-space preferably occurs prior to application of spatially encoding gradients 100 and 102 and again after application of rewinder gradients 106 and 108. Accordingly, in the illustrated pulse sequence, the origin of k-space is sampled twice each repetition time interval. Specifically, an A/D converter of MRI system 10, FIG. 1, is caused to be turned ON by the system control 32, FIG. 1, at moments 104 for the sampling of k-space origin. The A/D converter will remain ON 110 during readout, turn OFF 112 after readout, await application of rewinder gradients 106 and 108, and the briefly return to an ON state at 114. By sampling the origin of k-space before application of spatially encoding gradients and after rewinder gradients, it is possible to compare the data acquired at both instances to gain insight into the extent of motion during the acquisition of imaging data, i.e. during readout. Additionally, as will be described, the acquisition of the motion data in addition to the imaging data allows for dual purpose RF coils.

Figure 4:
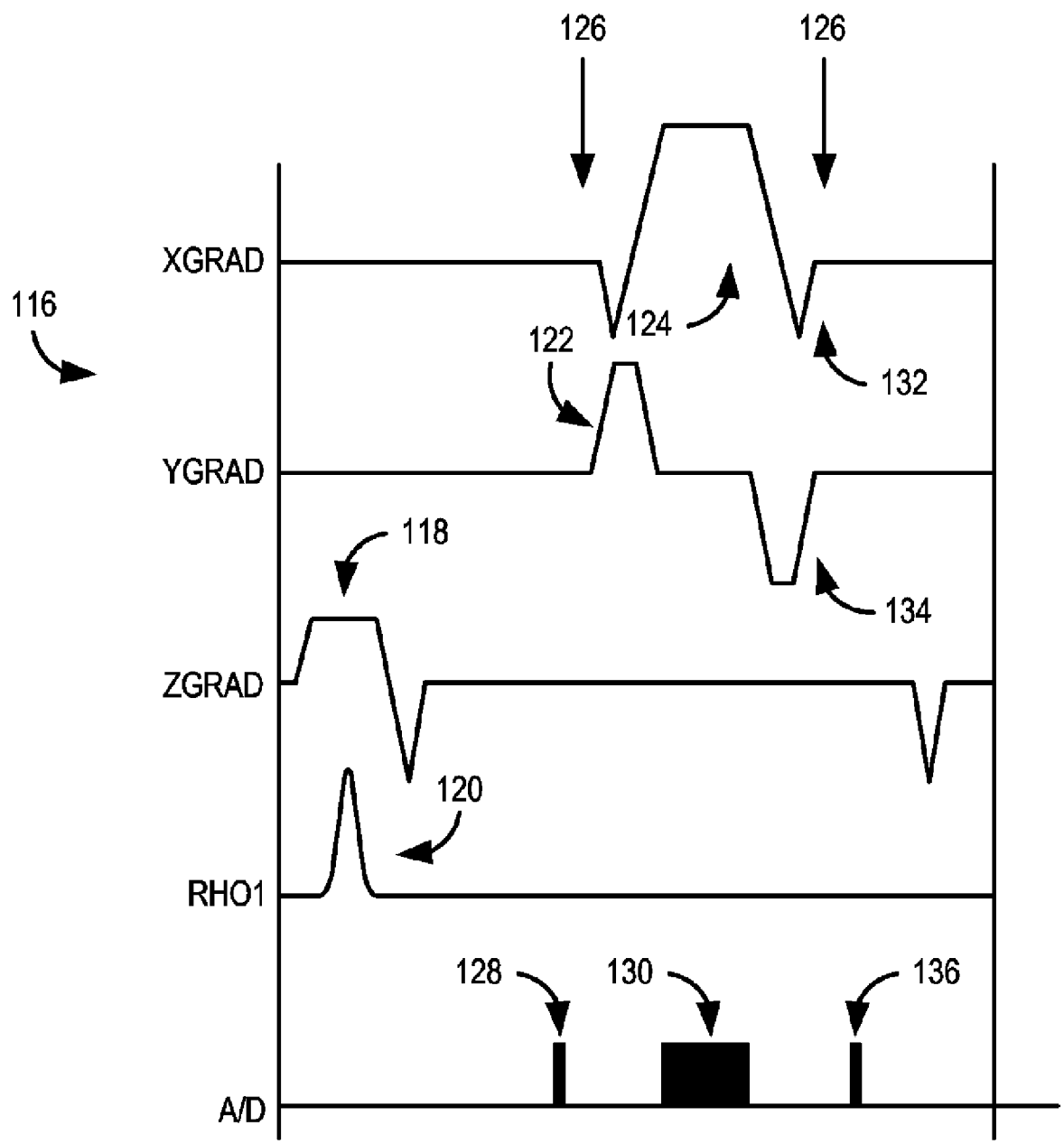
FIG. 4 is a pulse sequence diagram incorporating the present invention with a Cartesian SSFP k-space trajectory.

As described herein, the present invention is not dependent upon a given k-space trajectory. FIG. 3 illustrated a radial center-out k-space trajectory to which the present invention is applicable. FIG. 4 illustrates a Cartesian steady-state free precession (SSFP) pulse sequence 116. Pulse sequence 116 is defined by a slice select gradient 118 played out in the presence of an excitation pulse 120 to excite and encode a region-of-interest. The pulse sequence also includes a phase encoding pulse 122 and a frequency encoding or readout pulse 124. Again, arrows 126 indicate the instant of k-space origin traversal. The A/D converter samples the region-of-interest before application of the spatially encoding gradients at 128, during readout at 130, and after application of rewinder gradients 132, 134 at 136.

One skilled in the art will appreciate that neither pulse sequence 96 nor pulse sequence 116 employs additional gradient pulses to encode motion in the region-of-interest or excites additional echoes. In this regard, by appropriately timing of the A/D converter to sample the origin of k-space, motion data can be captured without requiring application of additionally time consuming gradients or exciting non-imaging echoes. As described above, the data corresponding to the origin of k-space can then be monitored for fluctuations in magnitude and/or phase to assess motion in the region-of-interest without a time penalty.

Figure 5:
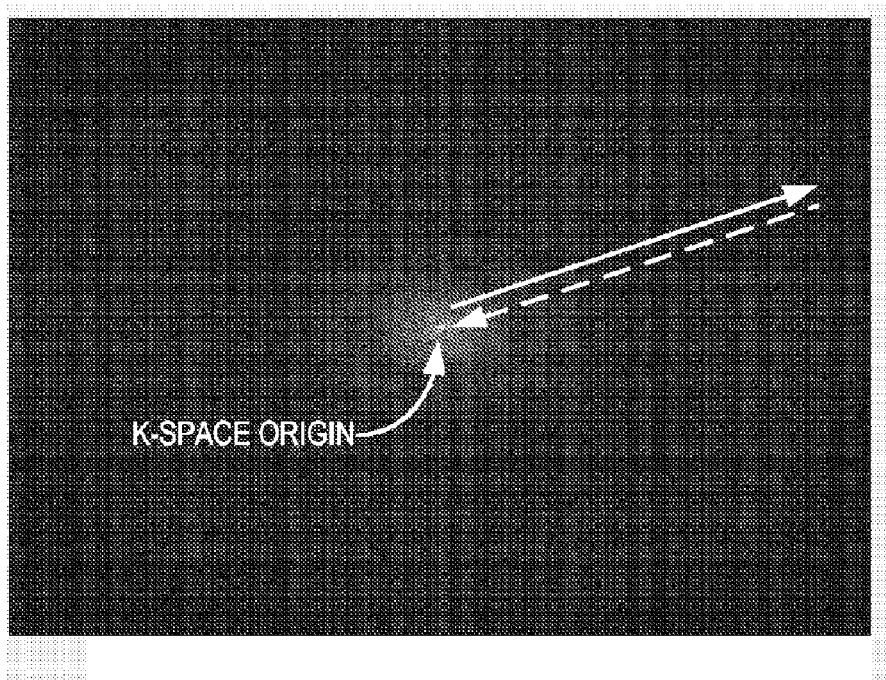
FIG. 5 is an image illustrating k-space traversal for the radial center-out pulse sequence of FIG. 3.
Figure 6:
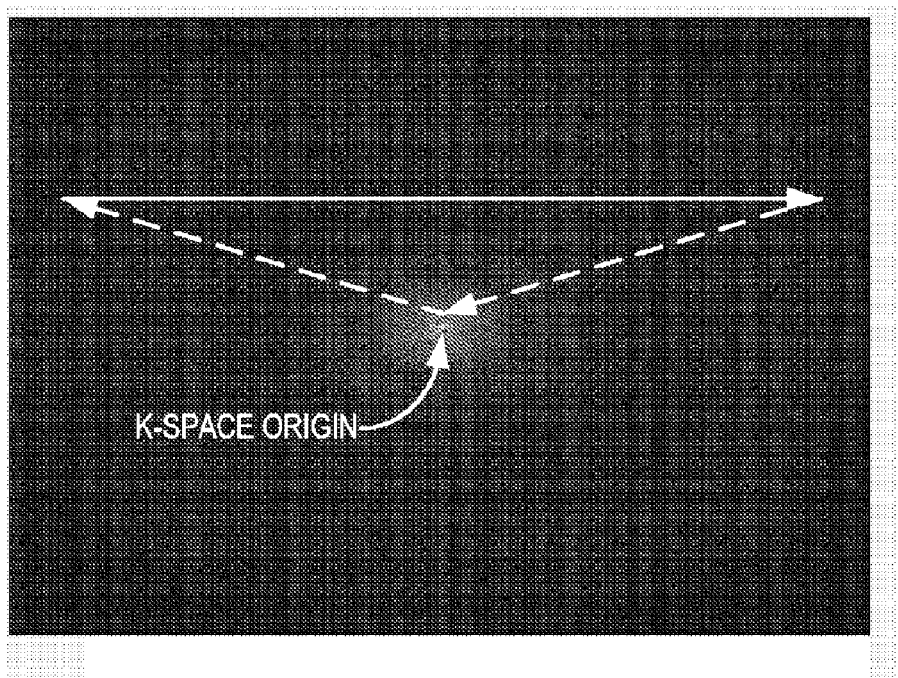
FIG. 6 is an image illustrating k-space traversal for the Cartesian SSFP pulse sequence of FIG. 4.

Referring now to FIGS. 5-6, k-space traversal corresponding to the radial center-out pulse sequence 96, FIG. 3, and the Cartesian SSFP pulse sequence 116, FIG. 4, are shown, respectively. Solid lines depict readout trajectories, while dashed lines depict prewinder and/or rewinder gradients. As illustrated, for both pulse sequences, the k-space trajectory starts and ends at the k-space origin, at which point motion encoded MR data can be acquired.

Figure 7:
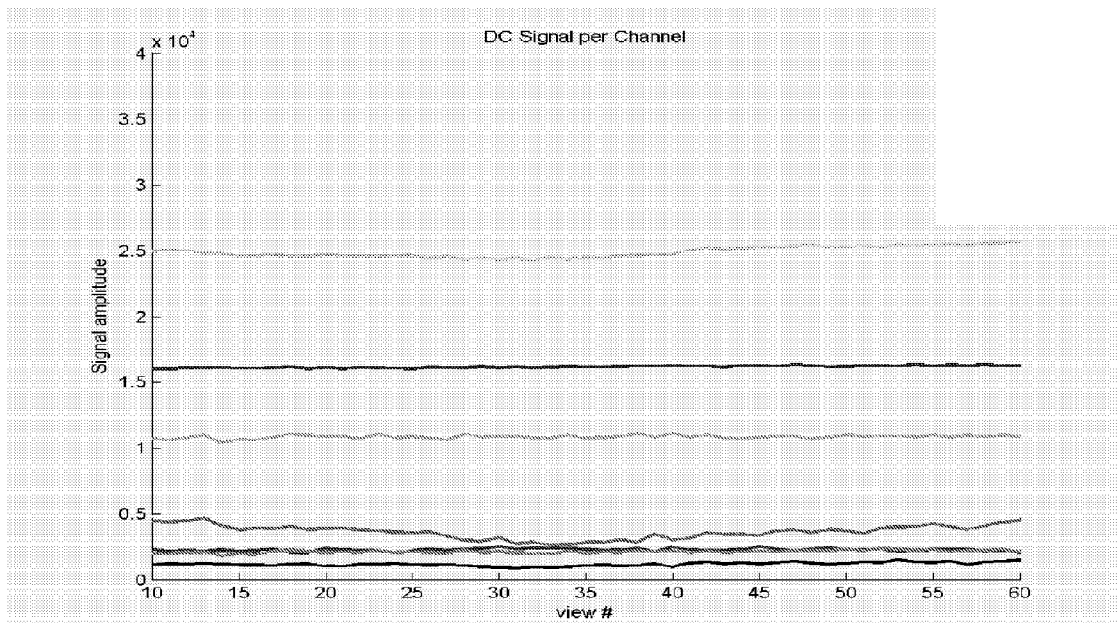
FIG. 7 is a graph that illustrates a comparison of k-space origin data for each channel of an eight channel cardiac coil during an axial phantom scan with no table motion.

As described herein, the present invention is applicable with single coil as well as multi-coil receivers. In this regard, the need for a "motion-only" coil designed to acquire motion data separate from an "imaging" data coil is eliminated. Simply, a coil used to acquire motion data is also used to acquire imaging data. Shown in FIG. 7 is a graph illustrating a comparison of k-space origin data recorded from each channel of an eight channel cardiac coil during an axial phantom scan with no table motion. As illustrated, fluctuations in the k-space origin data are relatively minor and, as such, motion in the region-of-interest is at a relatively steady-state over course of a scan.

Figure 8:
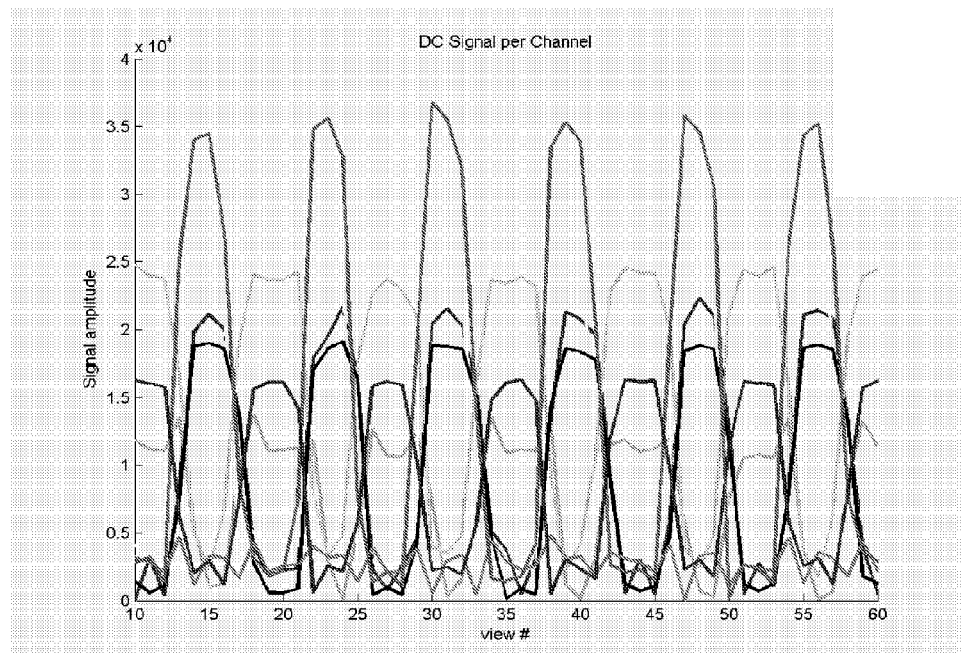
FIG. 8 is a graph comparing k-space origin data for each channel of an eight channel cardiac coil during an axial phantom scan with periodic table motion.

Conversely, and illustrated in FIG. 8, regular fluctuations in signal amplitude caused by through-plane phantom motion are visible for k-space origin data acquired with an eight channel cardiac coil during an axial phantom scan with periodic table motion (ten mm excursion every five seconds). Further, each channel (or coil) shows a different sensitivity to motion depending on its relative proximity to the excited region-of-interest. This variability in coil sensitivity, as described herein, can be exploited to characterize location and/or direction of motion when acquiring data with a multi-coil or phased-array assembly.

Figure 9:
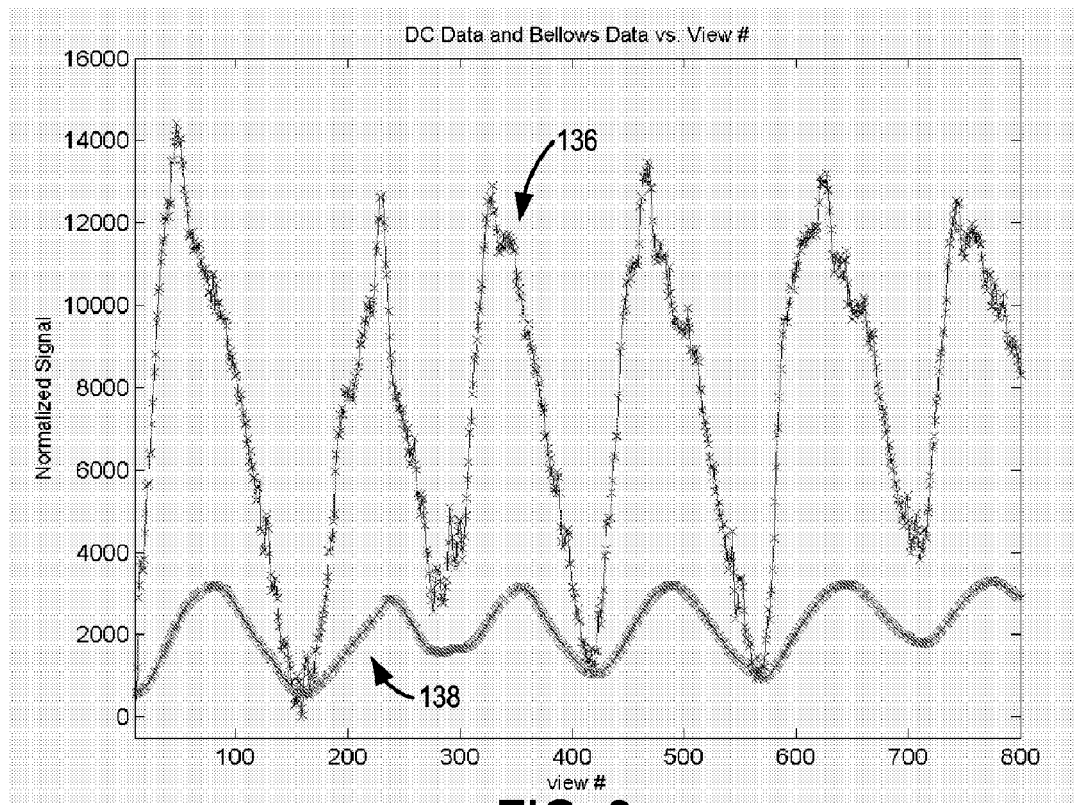
FIG. 9 is a graph comparing k-space origin data and respiratory bellows data from an axial liver scan in a free-breathing subject.

Referring now to FIG. 9, a comparison of k-space origin data 136 with respiratory bellows data 138 from an axial liver scan in a free-breathing subject is shown. K-space origin data 136 was acquired with a single channel of a phased-array coil. As illustrated, the k-space origin data tracks the respiratory bellows data 138 thereby indicating that breathing motion information can be extracted from the MR data at the origin of k-space without having to sample a separate respiratory bellows signal.

Figure 10:
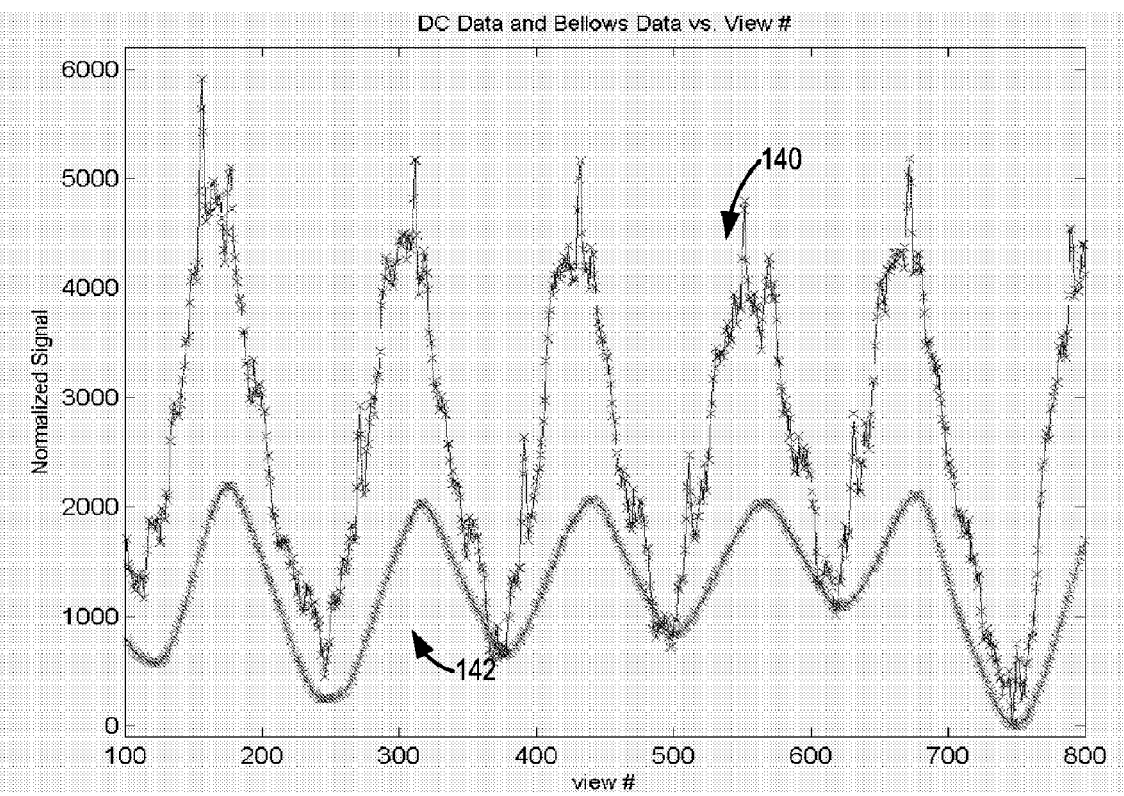
FIG. 10 is a graph illustrating a comparison of k-space origin data and respiratory bellows data during coronal liver imaging in a free-breathing subject.

Referring now to FIG. 10, a comparison of k-space origin data 140 with respiratory bellows data 142 acquired during a coronal liver scan of a free-breathing subject also shows a close correlation between motion encoded in the k-space origin data and the respiratory cycle of the free-breathing subject. As such, breathing motion information can be extracted from the MR data at the origin of k-space without having to sample a separate respiratory bellows signal.

Figure 11:
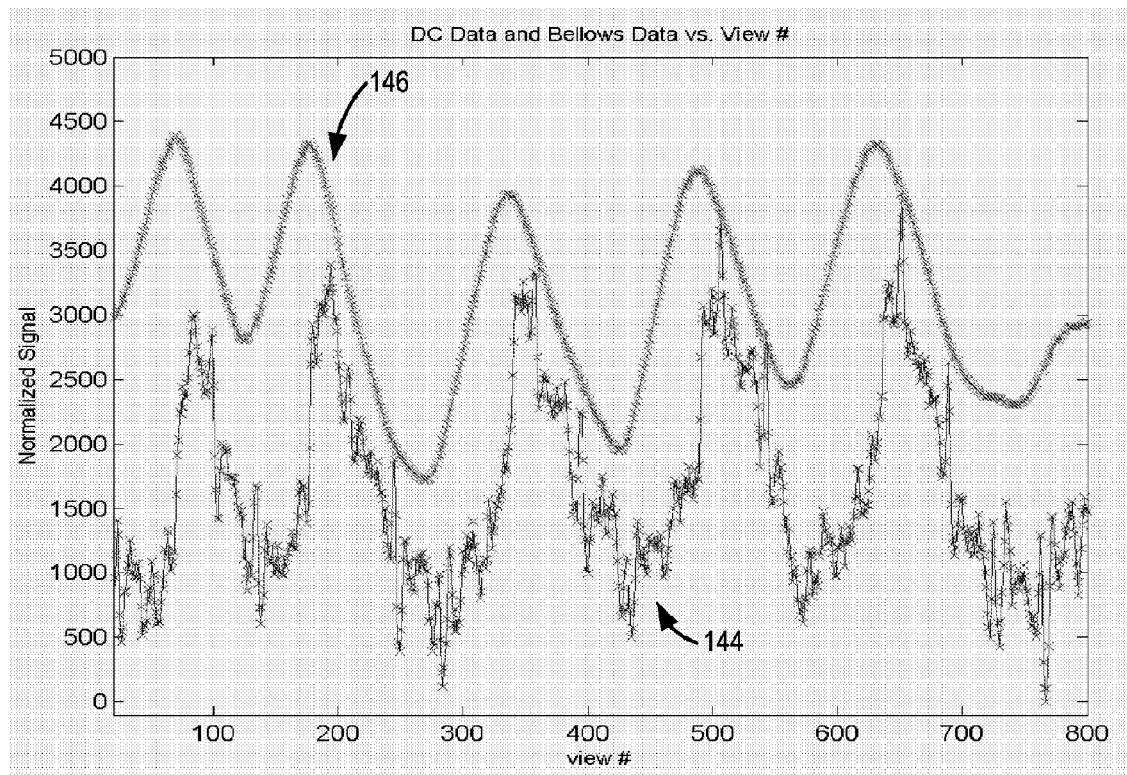
FIG. 11 is a graph illustrating a comparison of k-space origin data and respiratory bellows data during sagittal liver imaging in a free-breathing subject.

Referring now to FIG. 11, a comparison of k-space origin data 144 with respiratory bellows data 146 acquired during a sagittal liver scan of a free-breathing subject also shows a close correlation between motion encoded in the k-space origin data and the respiratory cycle of the free-breathing subject. As such, breathing motion information can be extracted from the MR data at the origin of k-space without having to sample a separate respiratory bellows signal. Further, FIGS. 9-11 illustrate the ability to carry out this extraction independent of a particular direction of readout.

Figure 12:
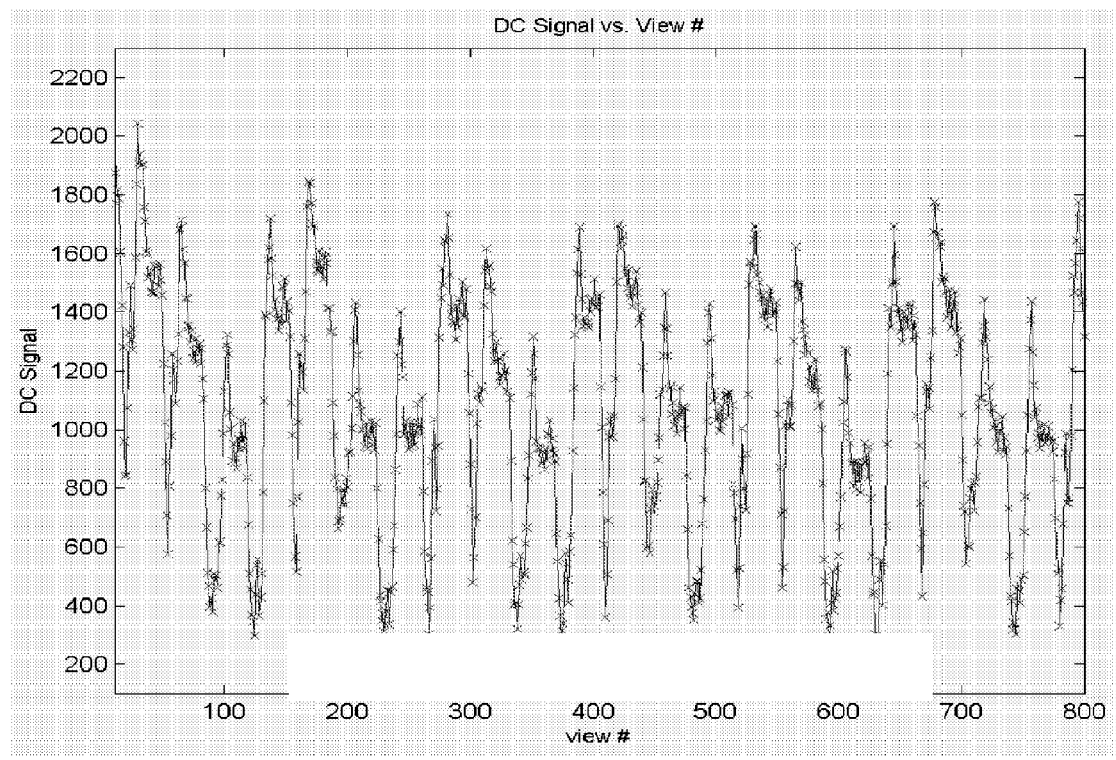
FIG. 12 compares k-space origin data extracted from an axial cardiac scan in a free-breathing subject.

FIG. 12 illustrates k-space origin data extracted from an axial cardiac scan in the free-breathing subject from which data was acquired for illustration in FIGS. 9-11. High frequency signal fluctuations matching the heart rate are visible. The fluctuations are the result of pulsatile cardiac motion in the subject. A slower frequency modulation of the data is also observed which can be attributed to breathing motion of the subject. In this regard, the present invention may be used to simultaneously gather both cardiac and respiratory motion information from the k-space origin data during cardiac imaging.

Figure 13:
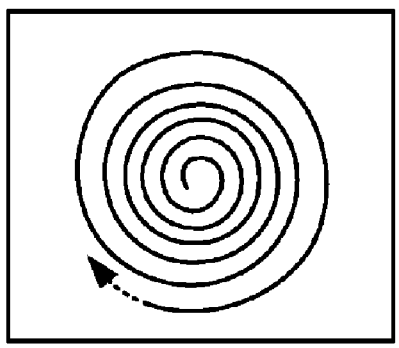
FIG. 13 is a schematic representation of a spiral k-space trajectory.
Figure 14:
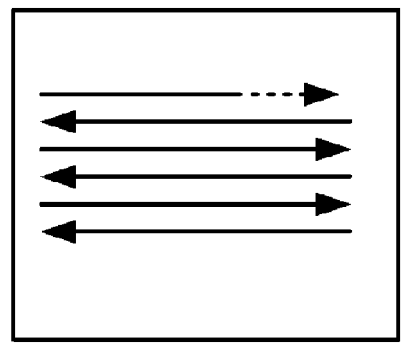
FIG. 14 is a schematic of a centric k-space trajectory.
Figure 15:
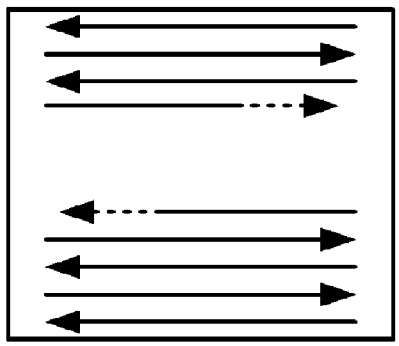
FIG. 15 is a schematic of a reverse-centric k-space trajectory.
Figure 16:
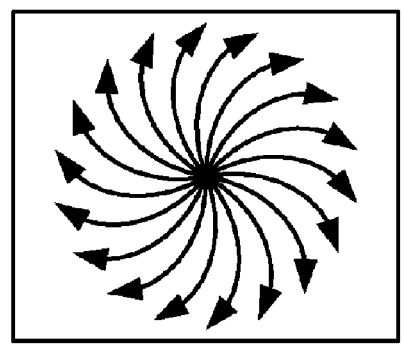
FIG. 16 is a schematic representation of a center-out k-space trajectory.

As described herein the present invention determines motion in a region-of-interest independent of the k-space trajectory employed to sample the region-of-interest. In this regard, the present invention is applicable with spiral, centric, reverse-centric, center-out, and other k-space filling schemes. A spiral k-space trajectory is illustrated in FIG. 13, a centric k-space trajectory is illustrated in FIG. 14, reverse-centric k-space trajectory is illustrated in FIG. 15, and a center-out k-space trajectory is illustrated in FIG. 16.

The present invention has been described with respect to the extraction of motion information within a region-of-interest directly from raw k-space data without implementation of separate physiological motion measuring systems. Moreover, by employing a direct extraction of motion information from k-space, the present invention provides a measurement of motion in the region-of-interest that is more accurate when compared to indirect techniques of assessing motion, i.e. ECGs. Additionally, the present invention is capable of ascertaining magnitude as well as phase information with respect to motion in a region-of-interest. In this regard, the present invention may be applied to not only improving synchronization of MR data in a gated acquisition, but also used in slice tracking and phase error correction. Furthermore, not only is the present invention k-space trajectory independent, it may also be implemented to assess multiple types of motion in a region-of-interest, such as respiratory, cardiac, and other anatomical induced motion. Moreover, the present invention is applicable with single coil and multi-coil receivers and, as such, can be used to differentiate location and direction of motion in an excited region based on coil sensitivity to the excited region. An understanding of location and direction of motion can further enable accurate assessment of motion in the region-of-interest for acquisition synchronization, slice tracking, and error correction.

The present invention is particularly applicable to body imaging scans where respiratory motion can severely limit image quality, especially in subjects who cannot hold their breath for extended periods of time. The present invention may also be applicable in cardiac imaging. In this regard, a separate ECG acquisition can be avoided and motion information derived directly from MR data can be used as a cardiac gating trigger for CINE imaging and other cardiac protocols. Detected respiratory motion of the heart could also be used to synchronize cardiac imaging with breathing or to perform slice tracking, particularly in coronary artery imaging applications, which are vulnerable to breathing motion.

Therefore, an MRI apparatus is disclosed and includes a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images. A computer is programmed to sample MR signals from a region-of-interest having motion therein with a given k-space trajectory to fill k-space and determine motion in the region-of-interest directly from sampled MR data acquired from the MR signals independent of the given k-space trajectory used to fill k-space.

The present invention also includes a method of MR imaging. The method includes sampling MR data over a plurality of repetition time intervals for a central region of k-space filled, using a given k-space filling trajectory, with MR data acquired from the region-of-interest having motion therein. The method also includes the steps of monitoring motion-induced modulation in the MR data for the central region of k-space over the plurality of repetition time intervals and determining motion in the region-of-interest from the motion-induced modulation independent of the given k-space filling trajectory.

The present invention may also be found in a computer readable storage medium having a computer program stored thereon to assess motion in a region-of-interest. The computer program includes a set of instructions that when executed by a computer causes the computer to sample a central region of k-space each repetition time interval of a pulse sequence applied to acquire MR data from the region-of-interest. The computer is then caused to measure modulation of MR data in the central region over several repetition time intervals. The computer is also caused to determine motion in the region-of-interest based on differences in magnitude and phase measured in the MR data over the several repetition time intervals independent of k-space trajectory used to sample the region-of-interest.

The present invention further includes a method of MR imaging that includes acquiring a first set of non-spatially encoded MR data from a region-of-interest prior to application of spatially encoding gradients and acquiring a second set of non-spatially encoded MR data from the region-of-interest after application of rewinder gradients. Motion in the region-of-interest is then determined from the first and the second set of non-spatially encoded MR data.

The present invention has been described in terms of the preferred embodiment, and it is recognized that equivalents, alternatives, and modifications, aside from those expressly stated, are possible and within the scope of the appending claims.

What is claimed is:

1. A magnetic resonance (MR) imaging apparatus comprising:
   an MR imaging system having a plurality of gradient coils positioned about a bore of a magnet to impress a polarizing magnetic field and an RF transceiver system and an RF switch controlled by a pulse module to transmit RF signals to an RF coil assembly to acquire MR images; and
   a computer programmed to:
      sample non-spatially-encoded MR data of a central region of k-space from a region-of-interest (ROI) using any given k-space trajectory, wherein the non-spatially-encoded MR data is sampled during a repetition time interval of a pulse sequence;
      sample spatially-encoded MR data from the ROI during the repetition time interval, wherein the spatially-encoded MR data comprises MR imaging data;
      sample additional non-spatially-encoded MR data of the central region of k-space from the ROI; and
      determine motion in the ROI based on MR motion data comprising the non-spatially-encoded MR data and the additional non-spatially-encoded MR data, wherein the MR motion data is free of MR imaging data.

2. The MR imaging apparatus of claim 1 wherein the central region of k-space comprises the center of k-space and a plurality of k-space points about the center of k-space.

3. The MR imaging apparatus of claim 1 wherein the computer is further programmed to:
determine a magnitude modulation among the non-spatially-encoded MR data and the additional non-spatially-encoded MR data; and
determine a gating signal based on the determination of the magnitude modulation to at least one of prospectively and retrospectively trigger a gated acquisition.

4. The MR imaging apparatus of claim 1 wherein the additional non-spatially-encoded MR data is sampled during the repetition time interval.

5. The MR imaging apparatus of claim 4 wherein the non-spatially-encoded MR data is sampled during the repetition time interval prior to the onset of a spatial encoding gradient to sample the spatially-encoded MR data, and wherein the additional non-spatially-encoded MR data is sampled after application of a rewinder pulse.

6. The MR imaging apparatus of claim 5 wherein the gated acquisition is at least one of a cardiac gated acquisition scheme and a respiratory gated acquisition scheme.

7. The MR imaging apparatus of claim 5 wherein the computer is further programmed to determine a modulation among the non-spatially-encoded MR data and the additional non-spatially-encoded MR data for the determination of the motion, wherein the modulation is at least one of a phase modulation and a magnitude modulation.

8. The MR imaging apparatus of claim 1 wherein the computer is further programmed to sample the additional non-spatially-encoded MR data during a repetition time interval subsequent to the repetition time interval in which the non-spatially-encoded MR data is sampled.

9. The MR imaging apparatus of claim 1 wherein the computer is further programmed to:
select an RF coil selected from the RF coil assembly that is most sensitive to the motion; and
sample the non-spatially-encoded MR data and the additional non-spatially-encoded MR data with only the selected RF coil.

10. The MR imaging apparatus of claim 1 wherein the non-spatially-encoded MR data, the additional non-spatially-encoded MR data, and the spatially-encoded MR data are sampled without subjecting a subject to breath-holding.

11. A computer readable storage medium having a computer program stored thereon, the computer program comprising a set of instructions that when executed by a computer cause the computer to:
acquire a first and a second set of central k-space magnetic resonance (MR) data from a region-of-interest (ROI) at a time other than during an application of frequency and phase encoding gradients, wherein at least the first set of central k-space MR data is acquired during a first repetition time of a pulse sequence;
acquire MR imaging data from the ROI during the first repetition time and during application of at least one of the frequency and phase encoding gradients;
assess motion in the ROI based on the first and second set of central k-space MR data, wherein the assessment of motion in the ROI is independent of the MR imaging data; and
reconstruct an MR image based on the assessment of motion.

12. The computer readable storage medium of claim 11 wherein the set of instructions cause the computer to acquire the second set of central k-space MR data during the first repetition time.

13. The computer readable storage medium of claim 11 wherein the set of instructions further cause the computer to correct at least one phase error in the MR imaging data based on the assessment of motion before reconstruction of the MR image.

14. The computer readable storage medium of claim 11 wherein the instructions that cause the computer to assess motion cause the computer to determine a DC fluctuation of at least one of a phase and magnitude among the first and second sets of central k-space data; and wherein the instructions further cause the computer to adjust a slice position based on the DC fluctuation.

15. A method of magnetic resonance (MR) imaging comprising:
sampling a central region of k-space associated with a region-of-interest (ROI) during a first repetition interval of a pulse sequence defined by an RF pulse using any k-space trajectory, wherein the sampling of the central region of k-space occurs prior to any application of spatial-encoding gradients during the repetition time interval such that a first non-spatially encoded data set is obtained;
sampling spatially-encoded MR data from the ROI during the first repetition interval;
determining motion in the ROI based on MR motion data, wherein the MR motion data comprises the first non-spatially encoded data set from the central region of k-space, and wherein the MR motion data is free of spatially-encoded MR data; and
reconstructing an MR image based on the determination of motion in the ROI.

16. The method of claim 15 further comprising:
sampling the central region of k-space associated with the ROI during the first repetition interval using the any given k-space trajectory to obtain a second non-spatially encoded data set; and
wherein determining the motion in the ROI comprises assessing at least one of magnitude and phase fluctuations among the first non-spatially encoded data set and the second non-spatially encoded data set, wherein the MR motion data further comprises the second non-spatially-encoded data set.

17. The method of claim 15 further comprising sampling the central region of k-space associated with the ROI during a second repetition interval using the any given k-space trajectory to obtain a second non-spatially encoded data set, wherein the MR motion data further comprises the second non-spatially encoded data set.

18. The method of claim 17 wherein determining the motion in the ROI comprises assessing at least one of magnitude and phase fluctuations among the first non-spatially encoded data set and the second non-spatially encoded data set, wherein the MR motion data further comprises the second non-spatially-encoded data set.

19. The method of claim 15 further comprising realigning the spatially-encoded MR data prior to reconstructing the MR image.

20. The method of claim 15 further comprising gating additional samplings of spatially-encoded MR data based on magnitude fluctuations, wherein gating additional samplings comprises at least one of cardiac gating and respiratory gating.

* * * * *